US006300509B1

(12) United States Patent
Crameri et al.

(10) Patent No.: US 6,300,509 B1
(45) Date of Patent: Oct. 9, 2001

(54) AMINO-AMIDE-RUTHENIUM COMPLEXES

(75) Inventors: Yvo Crameri, Oberwil; Kurt Püntener, Basel; Michelangelo Scalone, Birsfelden, all of (CH)

(73) Assignee: Roche Vitamins Inc., Parsippany, NJ (US)

( * ) Notice: Subject to any disclaimer, the term of this patent is extended or adjusted under 35 U.S.C. 154(b) by 43 days.

(21) Appl. No.: 09/705,412

(22) Filed: Nov. 3, 2000

Related U.S. Application Data

(62) Division of application No. 09/175,784, filed on Oct. 20, 1998, now Pat. No. 6,187,961.

(30) Foreign Application Priority Data

Nov. 6, 1997 (EP) .................................................. 97119381
Sep. 3, 1998 (EP) .................................................. 98116697

(51) Int. Cl.[7] ............................. C07F 15/00; C07C 45/65
(52) U.S. Cl. ............................................ 556/137; 568/366
(58) Field of Search .............................. 556/137; 568/366

(56) References Cited

U.S. PATENT DOCUMENTS

| | | | |
|---|---|---|---|
| 4,072,715 | 2/1978 | Boguth et al. | 260/586 R |
| 5,777,173 | 7/1998 | Paust et al. | 568/366 |

FOREIGN PATENT DOCUMENTS

| | | |
|---|---|---|
| 0 775 685 | 5/1997 | (EP) . |
| WO 97/20789 | 6/1997 | (WO) . |
| WO 98/42643 | 10/1998 | (WO) . |

OTHER PUBLICATIONS

H. Mayer, "Synthesis of Optically Active Carotenoids and Related Compounds," *Pure & Appl. Chem.*, vol. 51, pp. 535–564 (1979).
Leuenberger, et al., "Synthesis of Optically Active Natural Carotenoids and Structurally Related Compounds . . . ," *Helv. Chim. Acta.*, vol. 59, pp. 1832–1849 (1976).
Noyori, et al., "Asymmetric Transfer hydrogenation Catalyzed by Chiral Ruthenium Complexes," *Acc. Chem. Res.*, vol. 30, pp. 97–102 (1997).
Morandini, et al.,"Stereochemistry of Some Ligand Substitution and Insertion Reactions in Pseudotetrahedral Ruthenium (II) Complexes,"*Organometallics*, vol. 4, pp. 1202–1208 (1985).
Noyori, et al., Asymmetric Transfer Hydrogenation of Aromatic Ketones Catalyzed by Chiral Ruthenium (II) Complexes, *J. Am. Chem. Soc.*, vol. 117, pp. 7562–7563 (1995).
Noyori, et al., "Ruthenium (II)–Catalyzed Asymmetric Transfer Hydrogenation of Ketones Using a Formic Acid–Triethylamine," *J. Am. Chem. Soc.*, vol. 118, pp. 2521–2522 (1996).
Amundsen, et al.,"Certain Arylsulfonyl Derivatives of Ethylenediamine," *J.A.C.S.* 62, pp. 2811–2812 (1940).
Brunner, et al., *J. of Organometallic Chemistry* 456, pp. 71–75 (1993).
Simal, et al., *Tetrahedron Letters* 39, pp. 3493–3496 (1998).
Noyori et al, Angew.Chem.Int.Ed.Engl.,36 #3, pp. 285–287, 1997.*

* cited by examiner

*Primary Examiner*—Sreeni Padmanabhan
(74) *Attorney, Agent, or Firm*—Mark E. Waddell; Stephen M. Haracz; Bryan Cave LLP

(57) ABSTRACT

Amino-amide ruthenium complexes of the general formula RuH(L'{—H})(Y) and RuX(L'{—H})(Y) wherein X signifies chlorine, bromine or iodine, Y signifies a neutral ligand, L' signifies a monosulphonylated diamine of the general formula

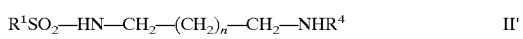

$R^1SO_2-HN-CH_2-(CH_2)_n-CH_2-NHR^4$         II'

$R^1$ signifies optionally mono- or multiply fluorinated alkyl, alkenyl, alkynyl, cycloalkyl, optionally mono- or multiply-substituted aryl, heteroaryl or camphor-10-yl, $R^4$ signifies hydrogen or alkyl, and n signifies 0, 1, 2 or 3.

is described.

5 Claims, No Drawings

AMINO-AMIDE-RUTHENIUM COMPLEXES

This is a divisional of U.S. application Ser. No. 09/175,784, filed Oct. 20, 1998, now U.S. Pat. No. 6,187,961.

FIELD OF THE INVENTION

The present invention is concerned with a process for the manufacture of trans-(R,R)-actinol by diastereoselective transfer hydrogenation in the presence of an amino-amide-ruthenium complex as the catalyst.

BACKGROUND OF THE INVENTION

Optically active actinol is known inter alia as an important building block for the synthesis of carotenoids such as zeaxanthin [Pure & Appl. Chem. 51, 535–564 (1979)]. In known processes actinol is manufactured from the trimethylcyclohexadione levodione. One such process is based, for example, on the catalytic hydrogenation of levodione in the presence of Raney nickel with a low base content [Helv. Chim. Acta 59, 1832 (1976)]. The poor diastereoselectivity of the heterogeneous hydrogenation, which leads to a 3–4:1 mixture of trans-and cis-actinol, results, however, in a loss in yield by virtue of the complicated purification; moreover there is a danger of a racemization of the levodione under the reaction conditions used in the heterogeneous catalysis. An alternative purification using a suitable distillation column is described in EP-A 0 775 685, but the yields are modest. The interest in manufacturing methods which yield actinol with high enantiomeric and diastereomeric purity is as great now as it always has been.

Processes for the manufacture of alcohols from ketones by transfer hydrogenation are known. Thus, for example, R. Noyori et al. [Acc. Chem. Res. 30, 97–102 (1997)] have investigated the asymmetric transfer hydrogenation of aryl alkyl ketones, such as, for example, acetophenone, which can be hydrogenated with high optical and chemical yield in the presence of a hydrogen donor, e.g. isopropanol/potassium hydroxide or acetic acid/triethylamine, and a ruthenium complex. However, not only the chemical yields, but also the optical yields diminish considerable when, for example, dialkyl ketones are used as substrates.

Surprisingly, it has now been found that (R)-levodione can be converted into (R,R)-actinol in good chemical yield and in high optical yield by transfer hydrogenation in the presence of an amino-amide-ruthenium complex.

SUMMARY OF THE INVENTION

The invention is accordingly concerned with a process for the manufacture of trans-(R,R)-actinol (1)

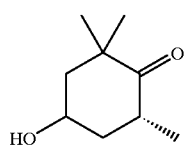

by the diastereoselective transfer hydrogenation of levodione by hydrogenating (R)-levodione (2)

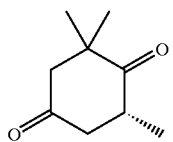

in the presence of a hydrogen donor, which simultaneously can be used as the solvent, and an amino-amide-ruthenium complex.

Specifically, this invention is directed to a process for the manufacture of trans-(R,R)-actinol (1)

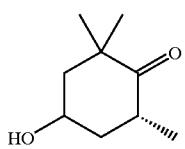

which process comprises hydrogenating (R)-levodione (2)

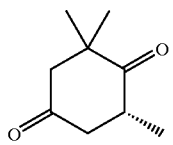

in the presence of a hydrogen donor and a solvent or in the presence of a hydrogen donor which is simultaneously used as the solvent, and an amino-amide-ruthenium complex.

A further process of this invention is the above process wherein the amino-amide-ruthenium complex has the formula $$RuH(L\{-H\})(Y) \qquad \qquad I$$

wherein
Y signifies a neutral ligand, and
L signifies a group of formula

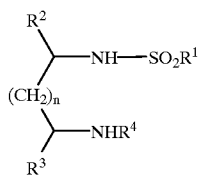

wherein
$R^1$ signifies alkyl which may be substituted with one or more fluorine atoms, alkenyl, alkynyl, cycloalkyl, aryl which may be substituted, heteroaryl, or camphor-10-yl,
$R^2$ and $R^3$ each independently signify hydrogen, alkyl, cycloalkyl, or aryl which may be substituted, or $R^2$ and $R^3$ together with $-CH-(CH_2)_n-CH-$ form a carbocycle with 4 to 8 carbon atoms,
$R^4$ signifies hydrogen or alkyl, and
n signifies 0,1,2 or 3.

The above process where $R^1$ is aryl or heteroaryl, and $R^2$ and $R^3$ are independently aryl, of which aryl is unsubstituted or substituted with phenyl, halogen, alkyl, or alkoxy, is also part of this invention, especially where $R^1$ as heteroaryl is a five- to six-membered heteroaryl with O as the heteroatom. The above process where $R^1$ is phenyl, tolyl, anisyl, or naphthyl is also part of this invention, as is the above process where Y is unsubstituted or substituted benzene.

DETAILED DESCRIPTION OF THE INVENTION

For the process in accordance with the invention there is preferably used an aminoamide-ruthenium complex of the general formula

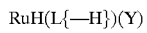

wherein
Y signifies a neutral ligand,
L signifies an optionally optically active, monosulphonylated diamine of the general formula

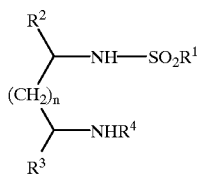

$R^1$ signifies optionally mono- or multiply-fluorinated alkyl, alkenyl, alkynyl, cycloalkyl, optionally mono- or multiply-substituted aryl, heteroaryl or camphor-10-yl, $R^2$ and $R^3$ each independently signify hydrogen, alkyl, cycloalkyl or optionally mono- or multiply-substituted aryl, or $R^2$ and $R^3$ together with the associated grouping —CH—(CH$_2$)$_2$—CH— form a carbocycle with 4 to 8 carbon atoms, $R^4$ signifies hydrogen or alkyl, and n signifies 0, 1, 2 or 3.

The monosulphonylated diamine is present in the complex as a monoanion and is accordingly denoted in formula I as "L{—H}".

In the scope of the present invention the term "substituted with one or more fluorine atoms", otherwise expressed as "mono- or multiply-fluorinated", means having at least one fluorine substituent to as many fluorines as the alkyl group so modified is capable of accepting; however one to five fluorines is preferred.

In the scope of the present invention the term "alkyl" embraces straight-chain or branched optionally chiral alkyl groups with 1 to 8 carbon atoms, preferably with 1 to carbon atoms. "Alkoxy" is an alkyl as defined above bonded by an oxygen atom. Methyl, ethyl, propyl, isopropyl, n-butyl, isobutyl, tert.butyl, n-pentyl and isopentyl are examples of alkyl groups. Similarly, methoxy, ethoxy, etc. are examples of alkoxy groups. Trifluromethyl, 2,2,2-trifluoroethyl and pentafluoroethyl are examples of mono- or multiply-fluorinated alkyl groups.

The term "alkenyl" embraces straight-chain or branched alkenyl groups with 3 to 8 carbon atoms, e.g. allyl, 2-butenyl and 3-butenyl.

The term "alkynyl" signifies a straight-chain or branched alkynyl group with one triple bond and 3 to 8 carbon atoms, e.g. propynyl and butynyl.

The term "cycloalkyl" signifies a 3- to 7-membered alicyclic group, namely cyclopropyl, cyclobutyl, cyclopentyl, cyclohexyl or cycloheptyl, of which cyclopentyl and cyclohexyl are preferred.

The term "unsubstituted or substituted aryl" or equally "aryl which may be substituted" or "optionally mono- or multiply-substituted aryl" preferably embraces a phenyl or naphthyl group, which can be unsubstituted, monosubstituted or multiply-substituted. As substitutents there come into consideration e.g. phenyl, halogen and straight-chain and branched alkyl and alkoxy groups with in each case 1 to 5 carbon atoms, whereby the multiply-substituted phenyl or naphthyl groups can have the same or different substituents. Of the alkyl and alkoxy groups the methyl and, respectively, methoxy group is preferred. Examples of optionally substituted aryl groups are phenyl, chloro-, bromo- and fluorophenyl, tolyl, anisyl, 2,4-dimethylphenyl as well as naphthyl.

The term "heteroaryl" embraces 5- or 6-membered heterocyclic groups featuring O, S or N as a ring member, i.e. heteroatom, such as, for example, furyl, thienyl, benzofuryl, dibenzofuryl, xanthenyl, pyrrolyl and pyridinyl. The heterocyclic groups featuring O as the heteroatom are especially preferred.

Under the term "neutral ligand" there is to be understood in the scope of the present invention an arene (an aromatic ring which may have an aliphatic side-chain), especially benzene, naphthalene or tetralin, which in the case of benzene is unsubstituted or substituted, in particular which can be mono- or multiply-substituted with straight-chain or branched alkyl and/or alkoxy groups with in each case 1 to 5 carbon atoms, preferably methyl or methoxy groups, and/or with cycloalkyl groups. Examples of such ligands are benzene, p-cymene, toluene, anisole, xylene, 1,3,5-trimethylbenzene, p-dicyclohexylbenzene, naphthalene and tetralin.

The (R)-levodione used as the starting material in the process in accordance with the invention can be obtained, as is known, inter alia by fermentation and is commercially available.

A particular class of amino-amide-ruthenium complexes used in any of the processes of this invention (especially a process where the amino-amide-ruthenium complex has formula I and L has formula II) consists of those of formula I which have a ligand of formula II in which $R^2$ and $R^3$ each independently signify hydrogen, alkyl, cycloalkyl or optionally mono- or multiply-substititued aryl (i.e. unsubstituted or substituted aryl) or $R^2$ and $R^3$ together with the associated grouping —CH—(CH$_2$)$_n$—CH— signifies a carbocycle (i.e. a hydrocarbon ring) with 4–6 carbon atoms, n signifies 0 or 1 and $R^1$ and $R^4$ have the significances given above.

In any process of this invention (especially a process where the amino-amide-ruthenium complex has formula I and L has formula II), preferred monosulphonylated diamine ligands L are those of formula II in which $R^2$ and $R^3$ have the same significance, e.g. are both either hydrogen or phenyl. Likewise preferred are the ligands L in which $R^2$ and $R^3$ together with the associated grouping —CH—(CH$_2$)$_n$—CH— form a carbocycle with 4 to 8 carbon atoms. In both cases $R^4$ preferably signifies hydrogen. Of these preferred ligands L there are especially preferred those in which n signifies 0.

Particularly preferred ligands L for any process of this invention (especially a process where the amino-amide-ruthenium complex has formula I and L has formula II) are the optically active monosulphonylated diamine ligands of formula II in which both $R^2$ and $R^3$ have a sigificance other than hydrogen, e.g. are independently alkyl, cycloalkyl, unsubstituted or substituted aryl, or together with —CH—(CH$_2$)$_n$—CH— form a carbocycle with 4 to 8 carbon atoms.

Irrespective of whether the monosulphonylated diamine ligands L are optically active or not, there are preferred those ligands L of formula II in which $R^1$ signifies a tolyl, anisyl or naphthyl group.

Examples of the particularly preferred monosulphonylated diamine ligands L for use in any process of this invention(especially a process where the amino-amide-ruthenium complex has formula I and L has formula II) are:

(1S,2S)-N-(2-Amino-1,2-diphenyl-ethyl)-4-methyl-benzenesulphonamide, (1R,2R)-N-(2-amino-1,2-diphenyl-ethyl)-4-methyl-benzenesulphonamide, (1RS,2RS)-N-(2-amino-1,2-diphenyl-ethyl)-4-methyl-benzenesulphonamide (racemic), (1S,2S)-N-(2-amino-1,2-diphenyl-ethyl)-4-methoxy-benzenesulphonamide, naphthalene-1-sulphonic acid [(1S,2S)-(2-amino-1,2-diphenyl-ethyl)-amide], (1R,2R)-N-(2-amino-cyclohexyl)-4-methyl-benzenesulphonamide, (1RS,2RS)-N-(2-amino-cyclohexyl)-4-methyl-benzenesulphonamide (racemic), N-(2-amino-ethyl)-4-methyl-benzenesulphonamide and N-(3-amino-propyl)-4-methyl-benzenesulphonamide.

For L in any process of this invention, in particular where the amino-amide-ruthenium complex has formula I and L has formula II, the meanings represented by the symbols $R^1$, $R^2$, $R^3$, $R^4$ and n in total present in the compounds listed immediately above represent preferred meanings for each of these symbols. For example, $R^1$ is preferably tolyl, anisyl or naphthyl, $R^2$ and $R^3$ are each preferably hydrogen or phenyl, or $R^2$ and $R^3$ together with the associated grouping —CH—(CH$_2$)$_n$—CH— preferably signifies the carbocycle with 6 carbon atoms (cyclohexane), n is preferably 0 or 1, and $R^4$ is preferably hydrogen. In preferred compounds, any combination of these preferred meanings is contemplated, for example where n is 0, $R^1$ is anisyl, $R^2$ is phenyl, $R^3$ is hydrogen, and $R^4$ is hydrogen, or the other alternatives provided by the above compounds.

While the first seven compounds are chiral, the eighth- and ninth-mentioned compounds are not chiral compounds.

For any of the processes of this invention (especially a process where the amino-amide-ruthenium complex has formula I and L has formula II) the transfer hydrogenation is conveniently effected in a solvent, which simultaneously serves as the hydrogen donor, or in a mixture of a hydrogen donor with a suitable inert solvent. As the hydrogen donor and at the same time the solvent there can be used especially alcohols, preferably secondary alcohols, e.g. isopropanol. As mixtures of hydrogen donors with an inert solvent there are conveniently used mixtures of alcohols with inert solvents, preferably a mixture of an alcohol with a lower aliphatic halogenated hydrocarbon, e.g. methylene chloride or ethylene chloride. Other suitable hydrogen donor/solvent mixtures are mixtures of formic acid or a salt thereof with an inert solvent, e.g. triethylamine. Isopropanol is particularly preferred as the hydrogen donor/solvent. In this case acetone is formed and this can, if desired, be removed continuously from the reaction system. When formic acid or a salt thereof in an inert solvent is used as the reducing agent, an about stoichiometric amount of formic acid or a salt thereof based on the amount of (R)-levodione is as a rule employed.

When mixtures of hydrogen donors with inert solvents are used, in principle all mixture ratios apply.

For any of the processes of this invention (especially a process where the amino-amide-ruthenium complex has formula I and L has formula 11), the ratio of catalyst (amino-amide-ruthenium complex) to (R)-levodione is conveniently about 1:20 to about 1:10,000 mol:mol, preferably about 1:200 to about 1:2000.

The diastereoselective transfer hydrogenation for any process of the invention (especially a process where the amino-amide-ruthenium complex has formula I and L has formula II) is conveniently effected at a temperature of about 0° C. to about 100° C., preferably of about 20° C. to about 50° C., and, if desired, under a protective gas, preferably argon. Moreover, as a rule it is performed under normal pressure or under a slight vacuum (in order, for example, to facilitate the removal of acetone formed from isopropanol).

Conventional methods of organic chemistry, e.g. distillation and crystallization, can be used for the isolation and purification of the thus-manufactured trans-(R,R)-actinol.

For any process of this invention (especially a process where the amino-amide-ruthenium complex has formula I and L has formula II), the amino-amide-ruthenium complex of formula I used as the catalyst for the diastereoselective transfer hydrogenation in accordance with the invention need not necessarily be employed as such, i.e. in its final form. Thus, it has been found practicable to generate the catalyst in situ in the reaction system, i.e. during the process of this invention, from the appropriate halogenated precursors (ruthenium-halogen complexes) described below (e.g. Scheme 1, compound (4)) which is effected according to the production processes described below. The amino-amide-ruthenium complexes of formula I are prepared for use as such, i.e. as the pre-prepared catalysts, or in situ as described below and in the Examples, preferably with the exclusion of oxygen.

The amino-amide-ruthenium complexes of formula I used as catalysts in accordance with the invention can be produced as outlined in Scheme I

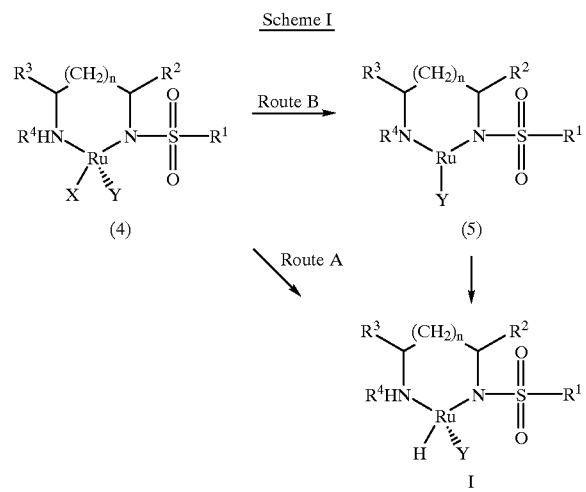

Scheme I

In Scheme I the symbols other than X have the aforementioned significances; X stands for chlorine, bromine or iodine, especially for chlorine.

In accordance with Route A the ruthenium catalysts of formula I are generated by reaction of the ruthenium-halogen complex of type 4 with a hydride donor, such as, for example, sodium formate or sodium methylate, in a solvent, e.g. in a lower alcohol or especially in the two-phase system methylene chloride/water. The reaction is conveniently carried out at room temperature. The complex formation has normally finished already after about 30 minutes. This is a method known per se for the conversion of Ru(II)-halogen complexes into Ru(II)-hydride complexes [see, for example, Principles and Applications of Organotransition Metal Chemistry, J. P. Collman et al., University Science Books (1987) and Organometallics 4, 1202 et seq. (1985)]. The ruthenium-halogen complexes of type 4 may be prepared by a skilled person from well-known reagents as described in these references and further references given hereinafter. They are especially suitable for the in situ production of the amino-amide-ruthenium complexes of formula I.

The ruthenium catalysts of formula I can also be obtained (Route B) by converting a ruthenium-halogen complex of type 4 with a base, such as, for example, sodium hydroxide or thallium ethylate, into the ruthenium-diamide complex of type 5 and subsequent reaction of the latter complex with an alcohol, e.g. isopropanol which simultaneously serves as the solvent. Mixtures of alcohols and/or water with an inert solvent, such as, for example, methylene chloride, can also be used as the solvent in this case. Also in this case, the reaction is conveniently carried out at room temperature and the complex formation is normally completed within 30 minutes.

Further information on these known methods and on the production of the ruthenium-halogen complexes of type 4 is contained in R. Noyori et al., J. Am. Chem. Soc. 117, 7562–7563 (1995), ibid., 118, 2521 (1996) and R. Noyori et al., Angew. Chemie 109 (3), 297 (1997). In these and other literature references, e.g. in PCT Patent Publication WO 97/20789, there are described some amino-amide-ruthenium complexes of formula I in which $R^2$ and $R^3$ each have a significance other than hydrogen (which accordingly have chiral centres) and their production in the above manner. The novel complexes of this class can be produced in an analogous manner.

A further method for the production of the amino-amide-ruthenium complexes of formula I used as catalysts in accordance with the invention is set forth in Scheme II hereinafter:

Scheme II: Route C $$[RuX_2(Y)]_2 + II + HCOONa + KOH \rightarrow I$$

In this Scheme X signifies chlorine, bromine or iodine. Y has the significance given above and II stands for the optionally optically active, monosulphonylated diamine of formula II (ligand L) given above. The reaction conditions (solvent, reaction temperature and reaction period), correspond to those for Route A and Route B.

The ligands L (of formula II) present in the above-described complexes are in part known compounds [see, for example, J.A.C.S. 62, 2811–2812 (1940)] and some of them are commercially available. Optically active diamines which are not commercially available can be obtained by resolution of the corresponding racemic diamines. The remaining (novel) ligands L can be produced analogously to the known ligands L.

Especially preferred amino-amide-ruthenium complexes of formula I for any process of this invention (especially a process where the amino-amide-ruthenium complex has formula I and L has formula II) are those in which the ligand L is N-(2-amino-ethyl)-4-methyl-benzenesulphonamide, N-(3-amino-propyl)-4-methyl-benzenesulphonamide, N-(2-amino-1,2-diphenyl-ethyl)-4-methyl-benzenesulphonamide or N-(2-amino-cyclohexyl)-4-methyl-benzenesulphonamide.

Those amino-amide-ruthenium complexes of formula I'

RuH(L'{—H})(Y)  I' in which L' signifies a monosulphonylated diamine of the general formula

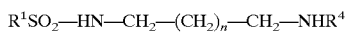

$$R^1SO_2\text{—HN—}CH_2\text{—}(CH_2)_n\text{—}CH_2\text{—}NHR^4 \quad II'$$

(i.e. of formula II wherein $R^2$ and $R^3$ are both hydrogen) and Y, $R^1$, $R^4$ and n have the significances given above for formula I, are novel and are likewise an object of the present invention. Because the two carbon atoms which carry the group NH—$SO_2R^1$ and, respectively, $NHR^4$ are not chiral, the diamine ligands of formula II' differ from those diamine ligands of formula II which have a substiutent at these positions ($R^2$ and $R^3$ each having a significance other than hydrogen). An example of such a complex is RuH(Ts-en{—H})(p-Cym). This stands for RuH(N-(2-amino-ethyl)-4-methyl-benzenesulphonamide{—H})(p-cymene).

The corresponding amino-amide-ruthenium complexes of the formula RuX(L'{—H})(Y), wherein X signifies chlorine, bromine or iodine, L' signifies a mono-sulphonylated diamine of formula II' and Y signifies a neutral ligand, are also novel and represent a further aspect of the present invention. Examples of such complexes are RuCl(Ts-en{—H})(p-Cym) and RuCl(Ts-en{—H})(hexamethylbenzene). These stand for RuCl(N-(2-amino-ethyl)-4-methyl-benzenesulphonamide{—H})(p-cymene) and RuCl(N-(2-amino-ethyl)-4-methyl-benzenesulphonamide{—H}) (hexamethylbenzene), respectively.

The following Examples illustrate the invention and in no manner represent any limitation. In these Examples the selected abbreviations have the following significances:

| | |
|---|---|
| Ts-DPEN | N-(2-Amino-1,2-diphenyl-ethyl)-4-methyl-benzenesulphonamide |
| (1-NaphthylS)-DPEN | Naphthalene-1-sulphonic acid(2-amino-1,2-diphenyl-ethyl)-amide |
| (p-AnS)-DPEN | N-(2-Amino-1,2-diphenyl-ethyl)-4-methoxybenzenesulphonamide |
| Ts-1,2-DACH | N-(2-Amino-cyclohexyl)-4-methyl-benzene-sulphonamide |
| Ts-en | N-(2-Amino-ethyl)-4-methyl-benzenesulphonamide |
| Ts-pn | N-(3-Amino-propyl)-4-methyl-benzenesulphonamide |
| p-Cym | p-Cymene |
| Me | Methyl |
| Et | Ethyl |
| TLC | Thin layer chromatography |
| GC | Capillary gas chromatography |
| ee | Enantiomeric excess |
| de | Diastereomeric excess |
| RT | Room temperature |

EXAMPLE 1

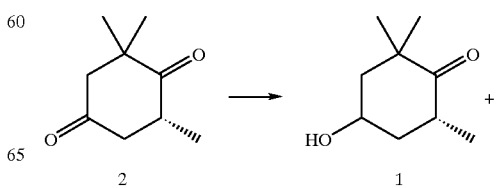

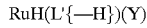

-continued

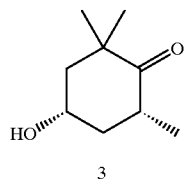

3

5.0 g (32.4 mmol) of (R)-levodione, 57 ml of isopropanol and 19.5 mg (0.0324 mmol) of [Ru((S,S)-Ts-DPEN{—2H}) (p-Cym)] were placed in a 185 ml steel vessel in a glove box ($O_2$ content <1 ppm). The steel vessel was closed and the transfer hydrogenation was carried out at 20° C. while stirring. The hydrogenation had finished (>99% conversion) within 24 hours. The hydrogenation solution was evaporated at 40° C./50 mbar (5 kPa) and the residue was distilled in a bulb-tube oven at 110° C./0.2 mbar (20 Pa). There were obtained 4.9 g of a mixture of 94%/5% (R,R)-actinol (1)/ (S,R)-actinol (3). The ee value of the (R,R)-actinol was 99.4%. The determination of the conversion, of the ee value and of the de value was effected by gas chromatography on a chiral phase (BGB-176: 2,3-dimethyl-6-tert.butyl-dimethyl-silylated-β-cyclodextrin).

EXAMPLE 2

100.0 g (0.648 mol) of (R)-levodione, 1.15 l of isopropanol and 0.389 g (0.648 mmol) of [Ru((S,S)-Ts-DPEN{—2H})(p-Cym)] were placed in a 2 l four-necked round flask and the transfer hydrogenation was started at 35° C. while stirring. The acetone which resulted during the hydrogenation was separated continuously while conducting argon through the reaction solution. The conversion was >99% after 8 hours. After working up analogously to Example 1 there were obtained 98 g of a mixture of 94%/6% (R,R)-trans-actinol/(S,R)-cis-actinol. The ee value of the (R,R)-trans-actinol was 99.3%.

EXAMPLES 3–14

The hydrogenations 3–14 were carried out in an analogous manner to Example 1 under the conditions given in Table 1:

EXAMPLE 15

Methods for the In Situ Production of the Catalysts Using [RuH(Ts-en{—H})(p-Cym)] as the Example All operations were carried out with the exclusion of oxygen.

Method A (Route A)

17.73 mg (0.26 mmol) of sodium formate and 63.10 mg (0.13 mmol) of [RuCl(Ts-en{—H})(p-Cym)] in 10 ml of methylene chloride and 1 ml of water were stirred vigorously at RT for 15 minutes. After phase separation the organic phase was washed three times with 10 ml of water each time and subsequently dried over anhydrous sodium sulphate.

Method B (Route A)

5.7 mg (0.08 mmol) of sodium formate and 20.2 mg (0.04 mmol) of [RuCl(Ts-en{—H})(p-Cym)] in 3 ml of methylene chloride and 3 ml of water were stirred vigorously at RT for 30 minutes. After subsequent phase separation the organic phase was dried over anhydrous sodium sulphate. Thereafter, 0.03 ml (0.4 mmol) of acetone was added and the mixture was stirred for 15 minutes.

Method C (Route B)

140.70 mg (0.29 mmol) of [RuCl(Ts-en{—H})(p-Cym)] and 72.5 mg (0.29 mmol) of thallium ethylate in 7 ml of isopropanol were stirred at RT for 30 minutes. The resulting precipitate was filtered off.

Method D (Route A)

3.88 mg (0.06 mmol) of sodium formate and 27.6 mg (0.06 mmol) of [RuCl(Ts-en{—H})(p-Cym)] in 5 ml of methanol were stirred at RT for 30 minutes.

Method E (Route A)

1.12 mg of sodium methylate and 11 mg of [RuCl(Ts-en{—H})(p-Cym)] in 5 ml of methanol were stirred at RT for 30 minutes.

EXAMPLE 16

11.3 g (73.5 mmol) of (R)-levodione were suspended in 130 ml of isopropanol in a two-necked round flask gassed with argon. The catalyst, prepared according to Example 15, Method A, from 71.2 mg (0.147 mmol) of [RuCl(Ts-en{—H})(p-Cym)] and 20.0 mg (0.294 mmol) of sodium formate, was added to the levodione suspension with the exclusion of air. The reaction had finished within 3 hours, the acetone resulting during the transfer hydrogenation being distilled off continuously while stirring at 25° C. The conversion was

TABLE 1

| Ex. | Arene (Y) | Diamine ligand (L) | T [° C.] | t [h] | S/C [m/m] | Conv. [%] | 1/3 | ee 1 [%] |
|---|---|---|---|---|---|---|---|---|
| 3 | p-Cym | (s,s)-Ts-DPEN | 20 | 4 | 200 | >99 | 95/4 | 99.7 |
| 4 | " | " | 30 | 3 | " | >99 | 94/5 | 99.8 |
| 5 | " | " | 40 | 2 | " | >99 | 94/5 | 99.8 |
| 6 | " | " | 50 | 2 | " | >99 | 93/6 | 99.8 |
| 7 | " | " | 20 | 3 | " | >99 | 94/4 | 99.6 |
| 8 | " | " | " | 3 | " | >99 | 94/5 | 99.4 |
| 9 | " | " | " | 3 | " | 98 | 91/6 | 99.1 |
| 10 | " | " | " | 3 | " | 97 | 89/7 | 98.8 |
| 11 | " | " | " | 24 | 500 | 99 | 93/6 | 99.4 |
| 12 | " | " | " | 24 | 1000 | 99 | 94/5 | 99.4 |
| 13 | " | (S,S)-(1-NaphthylS)-DPEN | 40 | 23 | 1000 | 79 | 75/4 | 99.4 |
| 14 | " | (S,S)-(p-AnS)-DPEN | 20 | 23 | 1000 | 96 | 91/6 | 99.3 |

S/C Substrate/catalyst (mol/mol)
Conv. Conversion 99.8 GC area %. After working up analogously to Example 1 there were obtained 10.9 g of a mixture of 96%/4% (R,R)-actinol/(S,R)-actinol. The ee value of the (R,R)-actinol was 98.1%.

EXAMPLES 17–29

The catalyst solutions were produced according to the methods (Meth.) described in Example 15. The transfer hydrogenations 17–29 were carried out analogously to Example 1 under the conditions given in Table 3:

TABLE 3

| | [RuH(L{-H})(Y)] | | | t | S/C | Conv. | | ee 1 |
|---|---|---|---|---|---|---|---|---|
| Ex. | L = | Y = | Meth. | [h] | [m/m] | [%] | 1/3 | [%] |
| 17 | (1RS,2RS)-Ts-DPEN | p-Cym | $ | 4 | 200 | 99 | 93/6 | 99.5 |
| 18 | (R,R)-Ts-DPEN | p-Cym | $ | 6 | 200 | 98 | 89/7 | 99.7 |
| 19 | (S,S)-Ts-DPEN | 1,3,5-Me$_3$-C$_6$H$_3$ | $ | 4 | 200 | >99 | 92/7 | 99.4 |
| 20 | (S,S)-Ts-DPEN | C$_6$H$_6$ | $ | 4.5 | 200 | >99 | 93/6 | 98.7 |
| 21 | (S,S)-Ts-DPEN | p-Cy$_2$-C$_6$H$_4$ | $ | 24 | 200 | 98 | 92/5 | 94.5 |
| 22 | (1RS,2RS)-Ts-1,2-DACH | p-Cym | C | 7 | 200 | >99 | 91/7 | 97.6 |
| 23 | (1RS,2RS)-Ts-1,2-DACH | p-Cym | A | 6 | 200 | 91 | 85/6 | 99.1 |
| 24 | (1RS,2SR)-Ts-1,2-DACH | p-Cym | A | 16 | 200 | 27 | 25/2 | 99.1 |
| 25 | Ts-en | p-Cym | C | 3 | 200 | >99 | 94/4 | 95.8 |
| 26 | Ts-en | p-Cym | A | 4 | 200 | >99 | 94/4 | 98.8 |
| 27 | Ts-en | p-Cym | D | 5 | 200 | 97 | 91/4 | 85.3 |
| 28 | Ts-en | p-Cym | B | 16 | 200 | >99 | 94/4 | 99.6 |
| 29 | Ts-pn | p-Cym | A | 22 | 20 | 76 | 68/8 | 96 |

All Examples were carried out at room temperature. The substrate concentration was 2% (weight percent).

$ The catalyst was produced, isolated and characterized in analogy to R.Noyori et al., Angew. Chem., 109, 297–300 (1997).

EXAMPLE 30

101 mg (0.21 mmol) of [RuCl(Ts-en{—H})(p-Cym)], 1.42 g (21.0 mmol) of sodium formate and 0.65 g (4.2 mmol) of (R)-levodione were suspended in 21 ml of dimethyl sulphoxide (DMSO) in a 50 ml Schlenk tube with the exclusion of oxygen and stirred at room temperature for 2 hours. A weak stream of argon was conducted through the suspension during this time. Subsequently, the Schlenk tube was closed and the suspension was stirred for a further 14 hours. Thereafter, 10 ml of water and 50 ml of methylene chloride were added and the two phases were separated. The aqueous phase was extracted twice with 50 ml of methylene chloride each time. The combined organic phases were dried over anhydrous sodium sulphate and evaporated on a rotary evaporator. According to GC analysis of the residue the conversion was 99.3% with a content of (R,R)-actinol of 91.2% (76.1% ee).

EXAMPLES 31–34

The hydrogenations 31–34 were carried out in an analogous manner to Example 30 under the conditions given in Table 4:

TABLE 4

| Ex. | [RuH(L{-H})(Y)] L = | Solvent | Hydride donor | C [M] | t [h] | Conv. [%] | 1/3 | ee 1 [%] |
|---|---|---|---|---|---|---|---|---|
| 31 | (R,R)-Ts-DPEN | Methanol | HCOONa | 0.2 | 2 | >99 | 94/6 | 90.5 |
| 32 | (R,R)-Ts-DPEN | DMSO | HCOONa | 0.2 | 6 | 85 | 81/4 | 96.2 |
| 33 | Ts-en | Methanol | HCOONa | 0.2 | 3 | >99 | 85/8 | 39.0 |
| 34 | (R,R)-Ts-DPEN | HCOOH/Et$_3$N (5:2) | HCOOH | 1 | 24 | 98 | 85/12 | 81.1 |

EXAMPLE 35

Production of the catalyst solution starting from [RuCl(Ts-en{—H})(p-Cym)]

A solution of 0.662 g (9.73 mmol) of sodium formate in 120 ml of water and a solution of 0.942 g (1.95 mmol) of [RuCl(Ts-en{—H})(p-Cym)] in 102 ml of methylene chloride were introduced into a sulphonation flask gassed with argon. The two-phase mixture was stirred intensively at 20–23° C. for 1 hour. The methylene chloride phase contained [RuH(Ts-en{—H})(p-Cym)], the active catalyst.

Transfer Hydrogenation 300.0 g (1.95 mol) of (R)-levodione were suspended in 3440 ml of isopropanol in a sulphonation flask while stirring at 20–25° C., the system was rendered inert with argon and the suspension was subsequently heated to 40° C. The methylene chloride phase containing the catalyst was added to the levodione solution with the exclusion of oxygen. The reaction solution was stirred at 40° C. under a partial vacuum of 150 mbar (15 kPa), with firstly the methylene chloride and then the acetone formed during the transfer hydrogenation being distilled off continuously. The acetone/isopropanol mixture distilled off was replaced by the addition of fresh isopropanol. The hydrogenation had finished after 6 hours. The conversion was 99.6 GC area %.

For the separation of the catalyst, the hydrogenation solution was evaporated, the residue was dissolved in diisopropyl ether and the solution was treated with active charcoal. After filtration and evaporation there were obtained 303.2 g of a mixture of 95%/5% (R,R)-/(S,R)-actinol as an oil. The ee value of the (R,R)-actinol was 98.9%. 100 g of this mixture were crystallized from diisopropyl ether/n-hexane. There were obtained 75 g of pure (R,R)-actinol with an ee >99.5%.

EXAMPLE 36

Production of the Catalyst Solution Starting from [RuCl$_2$(p-Cym)]$_2$ (Route C)

0.199 g (0.324 mmol) of [RuCl$_2$(p-Cym)]$_2$ and 0.139 g (0.648 mmol) of N-(p-tosyl)-ethylenediamine were dissolved in 20 ml of methylene chloride in a sulphonation flask gassed with argon and a solution of 0.221 g (3.25 mmol) of sodium formate and 0.036 g (0.64 mmol) of potassium hydroxide in 20 ml of water was added. The two-phase mixture was stirred intensively at 20–23° C. for 1 hour. The methylene chloride phase contained RuH(Ts-en{—H})(p-Cym)], the active catalyst.

Transfer Hydrogenation

The hydrogenation of 100.0 g (648.5 mmol) of (R)-levodione was effected analogously to Example 35. The hydrogenation had finished after 8 hours. There was obtained in >99% yield a mixture of 95%/5% (R,R)-actinol/(S,R)-actinol. The ee value of the (R,R)-actinol was 98.9%.

EXAMPLE 37

Production of [RuCl(Ts-en{—H})(p-Cym)]

50.0 g (0.233 mol) of N-p-(tosyl)-ethylenediamine and 71.5 g (0.117 mmol) of [RuCl$_2$(p-Cym)]$_2$ were dissolved in 650 l of methylene chloride, 330 l of water and 230 ml of 1M aqueous potassium hydroxide solution under argon in a 2 l sulphonation flask. The two-phase mixture was stirred vigorously at RT for 30 minutes. After phase separation the aqueous phase was back-extracted with 300 ml of methylene chloride and the combined organic phases were dried over anhydrous sodium sulphate. After filtration and evaporation the orange-red residue was digested in 400 ml of hexane and dried in a high vacuum. [RuCl(Ts-en{—H})(p-Cym)] was isolated as an orange solid in a yield of 97% (114.3 g). A 10 g sample was crystallized in methanol and 8.5 g of [RuCl(Ts-en{—H})(p-Cym)] were isolated as red crystals.

$^1$H-NMR (250 MHz, CDCl$_3$): 7.75 (d, 2H), 7.17 (d,2H), 5.7–5.3 (m, 5H), 3.2–2.1 (m br, 6H), 2.34 (s, 3H), 2.12 (s, 3H), 1.22 (d, 6H).

Microanalysis: Calc. for C$_{19}$H$_{27}$N$_2$O$_2$RuSCl (484.02): C 47.15; H 5.62; N 5.79; S 6.62; Cl 7.32; found C 47.21;H 5.64; N 5.80; S 6.40; Cl 7.23.

EXAMPLE 38

Production of [RuCl(Ts-en{—H})(Me$_6$C$_6$)]

Analogously to Example 37, after the reaction of 97.2 mg (0.4 mmol) of N-(p-tosyl)-ethylenediamine, 152.4 mg (0.2 mmol) of [RuCl$_2$(Me$_6$C$_6$)]$_2$ and 4.6 ml of 0.1M aqueous potassium hydroxide solution in water/methylene chloride and subsequent crystallization of the crude product in methanol there were isolated 106.0 mg (46%) of [RuCl(Ts-en{—H})(Me$_6$C$_6$)] as orange crystals.

$^1$H-NMR (250 MHz, CDCl$_3$): 7.80 (d, 2H), 7.11 (d, 2H), 3.5–3.2 (br, 2H), 2.5–2.2 (br, 4H), 2.31 (s, 3H), 2.17 (s, 18H).

Microanalysis: Calc. for C$_{21}$H$_{31}$N$_2$O$_2$RuSCl (512.07): C 49.26; H 6.10; N 5.47; S 6.26; Cl 6.92; found: C 49.03; H 5.96; N 5.51; S 6.02; Cl 6.86.

EXAMPLE 39

Production of [RuH(Ts-en{—H})(p-Cym)]

19.0 mg (0.04 mmol) of [RuCl(Ts-en{—H})(p-Cym)] and 26.7 mg (0.4 mmol) of sodium formate were dissolved in 2 ml of D$_2$O and 2 ml of CD$_2$Cl$_2$ under argon in a 5 ml Schlenk tube and the two-phase mixture was stirred at RT for 30 minutes. According to $^1$H-NMR analysis the yellow CD$_2$Cl$_2$ phase contained [RuH(Ts-en{—H})(p-Cym)] and a small amount of unreacted [RuCl(Ts-en{—H})(p-Cym)]. $^1$H-NMR (250 MHz, CD$_2$Cl$_2$): 7.46 (d, 2H), 7.09 (d, 2H), 5.0–4.5 (m, 4H), 3.0–1.5 (m,7H), 2.21 (s, 3H), 2.11 (s, 3H), 1.10 (d, 6H), −6.85 (s,1H).

What is claimed is:

1. Amino-amide-ruthenium complexes of the general formula

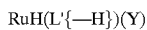

wherein

Y signifies a neutral ligand,

L' signifies a monosulphonylated diamine of the general formula

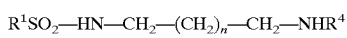

R$^1$ signifies optionally mono- or multiply fluorinated alkyl, alkenyl, alkynyl, cycloalkyl, optionally mono- or multiply-substituted aryl, heteroaryl or camphor-10-yl, R$^4$ signifies hydrogen or alkyl, and n signifies 0, 1, 2 or 3.

2. The amino-amide-ruthenium complex of claim 1 which is RuH(Ts-en{—H})(p-Cym).

3. Amino-amide-ruthenium complexes of the general formula

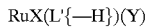

wherein

X signifies chlorine, bromine or iodine,

Y signifies a neutral ligand,

L' signifies a monosulphonylated diamine of the general formula

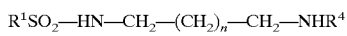

R$^1$ signifies optionally mono- or multiply-fluorinated alkyl, alkenyl, alkynyl, cycloalkyl, optionally mono- or multiply-substituted aryl, heteroaryl or camphor-10-yl R$^4$ signifies hydrogen or alkyl, and n signifies 0, 1, 2 or 3.

4. The amino-amide-ruthenium complex of claim 3 which is RuCl(Ts-en{—H})(p-Cym).

5. The amino-amide-ruthenium complex of claim 3 which is RuCl(Ts-en{—H})(hexamethylbenzene).

* * * * *